(12) United States Patent
Suzuki et al.

(10) Patent No.: US 9,157,990 B2
(45) Date of Patent: Oct. 13, 2015

(54) ULTRASONIC TRANSMITTING/RECEIVING CIRCUIT AND ULTRASONIC DIAGNOSTIC APPARATUS

(75) Inventors: Atsushi Suzuki, Tokyo (JP); Mitsuhiro Oshiki, Tokyo (JP); Kanako Hatayama, Tokyo (JP); Kenji Maio, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 1072 days.

(21) Appl. No.: 13/254,657

(22) PCT Filed: Mar. 1, 2010

(86) PCT No.: PCT/JP2010/053214
§ 371 (c)(1),
(2), (4) Date: Nov. 22, 2011

(87) PCT Pub. No.: WO2010/101104
PCT Pub. Date: Sep. 10, 2010

(65) Prior Publication Data
US 2012/0092954 A1    Apr. 19, 2012

(30) Foreign Application Priority Data
Mar. 4, 2009  (JP) .................................. 2009-050537

(51) Int. Cl.
*G01S 7/52* (2006.01)
*A61B 8/00* (2006.01)
(Continued)

(52) U.S. Cl.
CPC ........... *G01S 7/52079* (2013.01); *A61B 8/4444* (2013.01); *G01N 29/24* (2013.01);
(Continued)

(58) Field of Classification Search
CPC ............. A61B 8/4444; G01S 7/52079; G01N 2291/106; B06B 2201/76; G10K 11/341
See application file for complete search history.

(56) References Cited

U.S. PATENT DOCUMENTS 3,761,909 A * 9/1973 Schweitzer et al. ............ 367/94
4,109,644 A * 8/1978 Kojima ......................... 600/437
(Continued)

FOREIGN PATENT DOCUMENTS

| JP | 11-114494 | 4/1999 |
|---|---|---|
| JP | 2001-313552 | 11/2001 |

(Continued)

OTHER PUBLICATIONS

International Search Report for PCT International Application No. PCT/JP2010/053214, mailed Apr. 6, 2010.

*Primary Examiner* — Ari M Diacou
(74) *Attorney, Agent, or Firm* — Brundidge & Stanger, P.C.

(57) ABSTRACT

An ultrasonic transmitting/receiving circuit equipped with: a semiconductor circuit element which comprises at least three terminals including a first terminal connected to a plurality of transducer elements that constitute an ultrasonic probe, a second terminal connected to a transmission signal generating circuit, and a third terminal serving as an output terminal of an amplifier of a reception signal from the transducer element, and which has a function of amplifying a signal inputted from one terminal by the other terminal and outputting the amplified signal between at least two terminals among the above-said three terminals; and a control unit which performs control so as to cause the semiconductor circuit element to perform a first function of functioning as a switch for inputting a transmission signal to the transducer element and a second function of amplifying the reception signal received from the transducer element.

15 Claims, 4 Drawing Sheets

(51) Int. Cl.
  *G10K 11/34* (2006.01)
  *G01N 29/24* (2006.01)

(52) U.S. Cl.
  CPC .......... *G01S7/52017* (2013.01); *G10K 11/341* (2013.01); *A61B 8/54* (2013.01); *A61B 8/56* (2013.01); *B06B 2201/76* (2013.01); *G01N 2291/106* (2013.01)

(56) References Cited

U.S. PATENT DOCUMENTS

| | | | | |
|---|---|---|---|---|
| 4,202,215 A * | 5/1980 | Meyer | ............................ | 73/599 |
| 4,208,916 A * | 6/1980 | Thomenius et al. | ............ | 73/626 |
| 4,451,909 A * | 5/1984 | Kodera et al. | ................... | 367/99 |
| 4,520,830 A * | 6/1985 | Flanagan, III | ................ | 600/443 |
| 4,671,115 A * | 6/1987 | Ogawa et al. | ................... | 73/626 |
| 4,817,066 A * | 3/1989 | Takasugi et al. | .............. | 367/137 |
| 4,841,491 A * | 6/1989 | Kondo et al. | ................. | 367/103 |
| 4,872,145 A * | 10/1989 | Culbert et al. | .................. | 367/87 |
| 5,351,690 A * | 10/1994 | Okada et al. | .................. | 600/447 |
| 5,483,501 A * | 1/1996 | Park et al. | ...................... | 367/140 |
| 6,013,032 A * | 1/2000 | Savord | .......................... | 600/443 |
| 8,333,703 B2 * | 12/2012 | Kanda et al. | .................. | 600/459 |
| 2007/0016020 A1 * | 1/2007 | Oshiki et al. | .................. | 600/437 |
| 2008/0294055 A1 * | 11/2008 | Adachi et al. | ................. | 600/463 |
| 2009/0001853 A1 * | 1/2009 | Adachi et al. | ........... | 310/323.19 |
| 2014/0276075 A1 * | 9/2014 | Blalock | ......................... | 600/459 |

FOREIGN PATENT DOCUMENTS

| | | |
|---|---|---|
| JP | 2003-153898 | 5/2003 |
| JP | 2006-122449 | 5/2006 |
| JP | 2007-319286 | 12/2007 |
| JP | 2008-264342 | 11/2008 |

* cited by examiner (A)

(B)

(A)

(B)

ULTRASONIC TRANSMITTING/RECEIVING CIRCUIT AND ULTRASONIC DIAGNOSTIC APPARATUS

FIELD OF THE INVENTION

The present invention relates to an ultrasonic transmitting/receiving circuit which drives an ultrasonic probe and performs signal processing such as amplification of reception signals from the ultrasonic probe and an ultrasonic diagnostic apparatus using the same.

DESCRIPTION OF RELATED ART

An ultrasonic diagnostic apparatus is configured to transmit ultrasonic waves to an object to be examined from an ultrasonic probe, construct an ultrasonic image by an ultrasonic image construction unit with respect to a diagnostic region in the object using the reflected echo signals received by the ultrasonic probe, and display the constructed image on a display unit.

The ultrasonic probe transmits ultrasonic waves to the object via a plurality of transducers driven by an ultrasonic transmitting circuit of an ultrasonic transmission/reception unit, and receives the reflected echo signals from the object via the transducers by an ultrasonic receiving circuit of the ultrasonic transmission/reception unit.

The ultrasonic transmitting circuit applies a driving signal to the plurality of transducers in the ultrasonic probe so as to drive them, and performs reception signal processing such as amplification on the reflected echo signals. The transmission is performed by sine-wave signals or rectangular-wave signals being applied to the plurality of transducers of the ultrasonic probe. The voltage level of the signals upon transmission is, for example 100 Vpp and the frequency is between several MHz~20 MHz. The reception is performed by the reflected echo signals received by the ultrasonic probe being transmitted as electrical signals and the transmitted electrical signals being amplified. The voltage level of the reflected echo signals upon reception is several hundred mVpp and less, which is about a thousand times lower compared to the voltage level upon transmission. Due to such difference of the voltage level, the ultrasonic transmitting circuit and the ultrasonic receiving circuit have been respectively configured by different circuit elements. Furthermore, a transmission/reception separating circuit has been provided in order to electrically protect the ultrasonic receiving circuit by separating it from the ultrasonic transmitting circuit. Therefore, the ultrasonic transmission/reception unit has been formed by the ultrasonic transmitting circuit, ultrasonic receiving circuit and transmission/reception separating circuit, which made the circuit size of the ultrasonic transmission/reception unit large.

As a method for reducing the circuit size of the ultrasonic transmission/reception unit, the ultrasonic diagnostic apparatus having a switch for connecting and disconnecting to/from the power source of the reception signal amplifier in place of the transmission/reception separating circuit has been disclosed in Patent Document 1.

PRIOR ART DOCUMENT

Patent Document 1: JP-A-2007-319286

However, the demand for multi-channelizing of the transducers in the ultrasonic probe has not been satisfied by the conventional technique that merely reduces the parts count of circuits, which leaves the demand for a drastic reduction method.

The objective of the present invention is to provide an ultrasonic transmitting/receiving circuit capable of reducing the circuit size of the ultrasonic transmission/reception unit more than the conventional method.

Also, another objective of the present invention is to provide the ultrasonic diagnostic apparatus capable of reducing the circuit size of the ultrasonic transmission/reception unit more than the conventional method.

BRIEF SUMMARY OF THE INVENTION

In order to achieve the above-described objective, the ultrasonic transmitting/receiving circuit related to the present invention comprises:

a semiconductor circuit element which has at least three terminals including a first terminal connected to a plurality of transducer elements that constitute an ultrasonic probe, a second terminal connected to a transmission signal generating circuit and a third terminal serving as an output terminal of an amplifier of a reception signal from the transducer element, and has a function to amplify the signal inputted to one terminal by the other terminal and outputting the amplified signal between at least two terminals among the above-mentioned three terminals; and a control unit configured to control the semiconductor circuit so as to respectively perform a first function as a switch for inputting a transmission signal to the transducer element and a second function of amplifying the reception signal from the transducer element.

In accordance with the ultrasonic transmitting/receiving circuit, since the control unit causes the semiconductor circuit element to perform the first function and the second function respectively, it is possible to reduce the circuit size of the ultrasonic transmission/reception unit more than the conventional technique.

In order to achieve another objective described above, the ultrasonic diagnostic apparatus of the present invention comprises:

an ultrasonic probe configured to transmit/receive ultrasonic waves to/from an object to be examined;

an ultrasonic transmission/reception unit configured to drive the ultrasonic probe and perform signal processing on the reflected echo signal received from the ultrasonic probe;

an ultrasonic image construction unit configured to construct an ultrasonic image using the signal-processed reflected echo signals;

a display unit configured to display the ultrasonic image;

a control unit configured to control the respective units from the ultrasonic probe to the display unit; and a setting unit configured to set control condition of the respective units in the control unit, wherein:

the ultrasonic transmission/reception unit has a semiconductor circuit element which has at least three terminals including a first terminal connected to a plurality of transducer elements that constitute an ultrasonic probe, a second terminal connected to a transmission signal generating circuit and a third terminal serving as an output terminal of an amplifier of a reception signal from the transducer element, and has a function to amplify the signal inputted to one terminal by the other terminal and outputting the amplified signal between at least two terminals among the above-mentioned three terminals; and the control unit controls the semiconductor circuit so as to perform a first function as a switch for inputting a transmission signal to one channel of the transducer element and a second function of amplifying the reception signal received from one channel of the transducer element.

In accordance with the ultrasonic diagnostic apparatus of the present invention, since the control unit causes the semiconductor circuit element to perform the first function and the second function respectively, it is possible to reduce the circuit size of the ultrasonic transmission/reception unit more than by the conventional technique.

EFFECT OF THE INVENTION

In accordance with the present invention, it is possible to provide the ultrasonic transmitting/receiving circuit capable of reducing the circuit size of the ultrasonic transmission/reception unit more than the conventional technique, and the ultrasonic diagnostic apparatus using the same.

BRIEF DESCRIPTION OF THE DIAGRAMS

DETAILED DESCRIPTION OF THE INVENTION

An embodiment of the present invention will be described in detail below.

Figure 1:
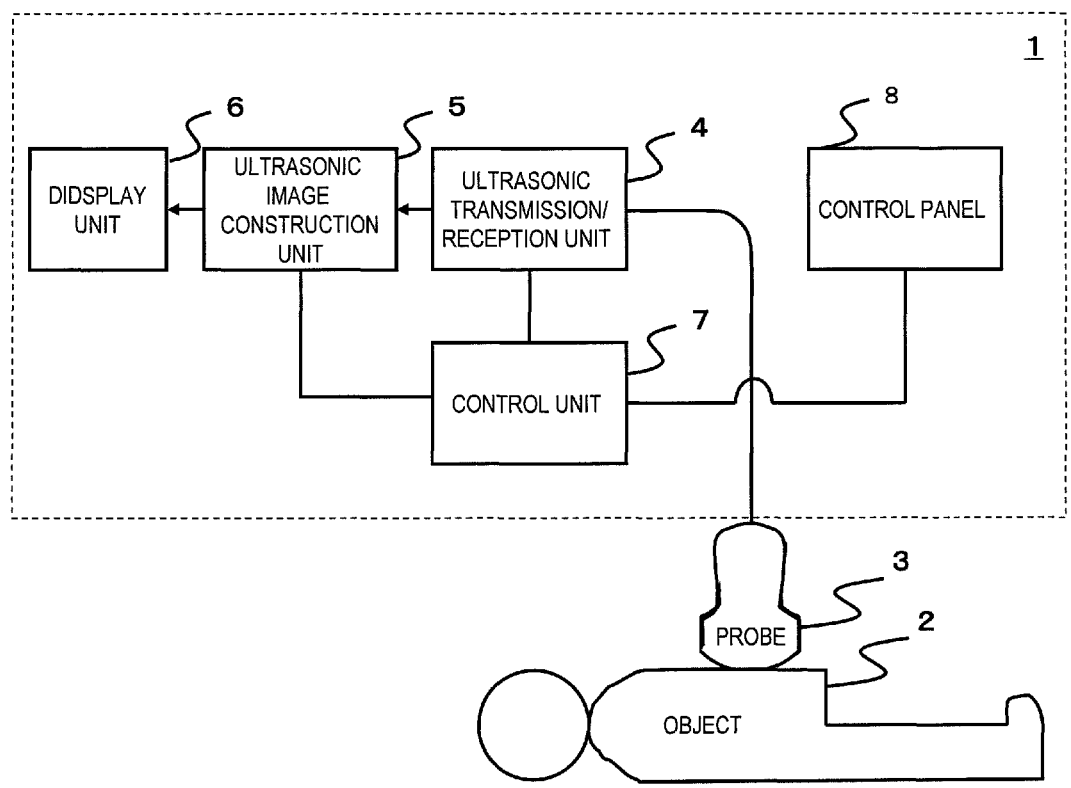
FIG. 1 is a block diagram showing the configuration of the ultrasonic diagnostic apparatus to which the present invention is applied.

FIG. 1 is a block diagram showing the configuration of the ultrasonic diagnostic apparatus to which the present invention is applied.

An ultrasonic diagnostic apparatus 1 constructs and displays an ultrasonic image with respect to a diagnostic region in an object 2 to be examined using the reflected echo signals acquired by transmitting/receiving ultrasonic waves to/from the object. The ultrasonic diagnostic apparatus 1 comprises an ultrasonic probe (abbreviated as a probe in FIG. 1) 3, an ultrasonic transmission/reception unit 4, an ultrasonic image construction unit 5, a display unit 6, a control unit 7 and a control panel 8.

The ultrasonic probe 3 irradiates ultrasonic waves to the object 2, receives the reflected echo signals from the object 2, and has plural channels of transducer elements. The ultrasonic transmission/reception unit 4 has both functions including the function as the ultrasonic transmission unit which drives ultrasonic probe and irradiates ultrasonic waves, and the function as the ultrasonic reception unit which amplifies the reflected echo signals received by the ultrasonic probe 3. The ultrasonic image construction unit 5 constructs an ultrasonic image based on the reception signals. Display unit 6 displays the ultrasonic image constructed in the ultrasonic image construction unit 5. The control unit 7 is, for example a CPU of the computer system which controls the respective components of the ultrasonic probe 3, the ultrasonic transmission/reception unit 4, the ultrasonic image construction unit 5 and the display unit 6. The control panel 8 is a keyboard or pointing device wherein an operator provides a control parameter to the control unit 7.

Embodiment 1

A configuration example and operation example of the ultrasonic transmission/reception unit in the first embodiment related to the present invention will be described referring to FIG. 2.

Figure 2:
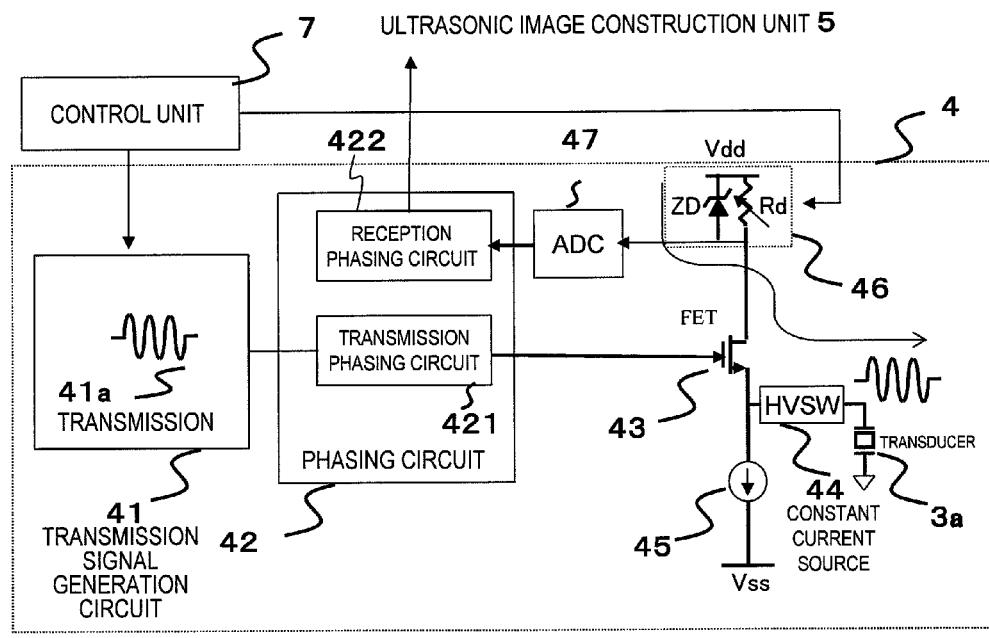
FIG. 2 is a circuitry diagram and an operation diagram of a first embodiment related to the present invention.
Figure 2:
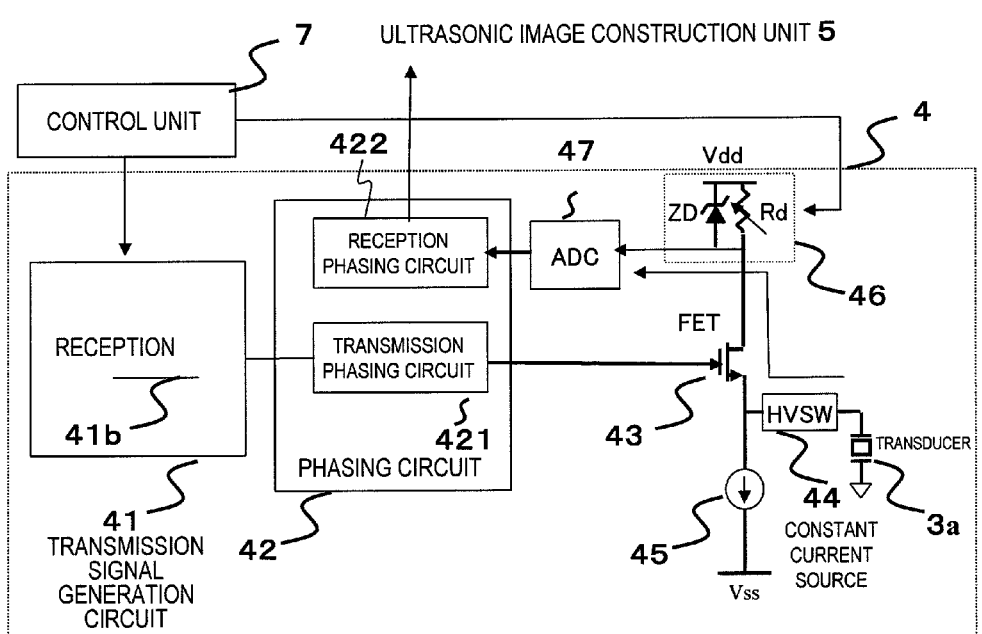

FIG. 2 is a circuitry diagram and operation diagram of the first embodiment related to the present invention. FIG. 2(A) shows an operation diagram upon transmission of an ultrasonic wave, and FIG. 2(B) shows an operation diagram upon receiving an ultrasonic wave.

The ultrasonic transmission/reception unit 4 includes a transmission signal generating unit 41, a phasing circuit 42, a field-effect transistor (FET) 43, a high-voltage switch (HVSW) 44, a constant current source 45, a sensitivity control circuit 46 and an analogue digital converter (ADC) 47.

The transmission signal generating unit 41 generates the transmission signals to provide them to the respective channels of the transducer elements in the ultrasonic probe. The transmission signal is an arbitrary alternating-current signal such as a rectangle-wave signal. In the present invention, the transmission signal generating unit 41 receives the signal in the condition that an ultrasonic wave is being transmitted or received from the control unit 7, provides the alternating-current signal to a gate terminal of an FET 43 upon transmission, and provides the direct-current signal to a gate terminal of the FET 43 upon reception. A transmission signal generating unit 41 may also be configured by a memory such as a ROM that generates transmission waveforms.

The phasing circuit 42 is for an operator to focus an ultrasonic signal (reflected echo signal) to the depth for acquiring a desired ultrasonic image of the object, and includes a transmission phasing circuit 421 and a reception phasing circuit 422. Here, the depth is different depending on the kind of the ultrasonic probe used by the operator or the target organ of the object for diagnosis, thus controlled by, for example the control panel 8. The transmission phasing circuit 421 is for focusing the ultrasonic signal to be transmitted, and the reception phasing circuit 422 is for focusing the reflected echo signal. The phasing method of the phasing circuit 42 may be either of the analogue phasing method that phases the ultrasonic signal as is the analogue signal or the digital phasing method that phases the ultrasonic signal which is the analogue signal by digitalizing it. A major example of phasing circuit 42 is disclosed in JP-A-2008-264342. In addition, when the reflected echo signal is to be digitalized to make it into the reflected echo data, the phasing is to be executed on the digital data.

For the FET 43, the NMS-type is to be used which is advantageous for integration of circuits. The reason for choosing NMOS-type FET 43 is that the carrier of NMOS-type FET is an electron having the smaller effective mass than an electron hole of the PMOS-type, which facilitates high-speed transmigration of the carrier and high-speed operation, and that the occupancy area of the FET element itself of the NMOS-type is also smaller compared to that of the PMOS-type.

Also, while the case of using the NMOS-type is exemplified in the first embodiment, practically the same function as using the NMOS-type can be accomplished by using the PMOS-type or the complementary type in which the NMOS-type and the PMOS-type are combined.

The FET 43 has a function that receives the input of its own gate terminal and inputs the AC voltage in the form of a sine-wave or a rectangular wave to the gate terminal upon transmission, and outputs the AC voltage to one channel of the transducers constituting the ultrasonic probe 3 from its own source terminal (a first function) . Since the FET 43 configures the source follower circuit, the transmission waveform applied to the gate terminal is outputted to the source terminal as it is. The characteristic of the source follower circuit is that the input impedance becomes high and the output impedance becomes low. The input impedance being high has the advantage that the effect of using the circuit can be reduced, and the output impedance being low has the advantage that more loads (transducers) can be driven.

Also, the FET 43 has a function that receives the input of its own gate terminal and inputs the DC voltage to the gate terminal upon reception, inputs the reflected echo signal outputted from 1 channel of the transducers to be the amplifier element of the gate grounding amplifier circuit, and outputs the amplified reflected echo signal to the ADC 47 from its own drain terminal (a second function).

The transmission gate of the gate grounding amplifier can be substantively expressed as the expression 1 by multiplying equivalent conductance gm of the FET 43 itself and the variable resistor Rd in the sensitivity control circuit 46.

[Expression 1]

Transmission gate of a gate grounding amplifier circuit of an amplifier≅gm*Rd

The gate grounding amplifier circuit fixes the voltage of the gate terminal of the FET 43 at a certain DC voltage (also referred to as a "bias voltage"), sets the source voltage of the FET 43 as the input terminal of the amplified signal, and uses the drain terminal of the FET 43 to which load resistance Rd is connected as the output terminal of the amplifying signal. When the changed portion of the voltage of the source terminal which is the input terminal rises for the portion of Vin, since the voltage between the gate-sources of the NMOS-type transistor falls, changed portion Vo of the output voltage becomes the same phase as Vin.

Also by changing the value of the variable resistor Rd, the transmission gate of the amplifier of the gate grounding amplifier circuit becomes variable. The control unit 7 is capable of controlling the value of variable resistor Rd by the display depth of an ultrasonic image of the object. The transmission gate of the amplifier of the gate grounding amplifier circuit is proportional to the magnitude of the variable resistor Rd.

The high-voltage switch (HVSW) 44 is connected to the source terminal of the FET 43, and supplies the output of one of the transmission signal generating units 41 to a plurality of transducer elements in order to provide the signal to the entire elements of the transducers. The HVSW 44 is to be used in the case that the number of entire elements of the driven transducers in the probe is different from the number of circuits.

The reason for disposing the switch is, in the case that a plurality of transducer elements are arranged symmetrically, that the number of the transmission signal generating circuits 41 for supplying the transmission signals from the transmission phase circuit 421 can be made half of the number of transducer elements, as to be described in the following illustrative example.

In concrete terms, eight transducer elements are arranged horizontally in a row, and when the transducer elements are numbered by numerals of 31~38 in order from the left, the elements of the pair of both ends are 31 and 38, and the elements of the pair of the respectively inner side by one element are 32 and 37, the elements of the pair of further inner side by one element are 33 and 36, and the elements of the most inner sides of the pair are 34 and 35 (not shown in the diagram). If the ultrasonic beams to be transmitted from the transducer elements can be disposed in any way as long as they are axisymmetric from the center portion in the row of the transducer elements, the same transmission signal may be provided from the transmission signal generating circuit 41 to the above-described respective pairs. In other words, it is not necessary to provide eight transmission signal generating circuits 41 which is the same number as the transducer elements, but only four which is half the number of transducers is sufficient. Also, the actual number of transducer elements is greater such as 96, 128 or 192 channels, and the array direction of the transducer elements is two-dimensional. Since the multichannel technology in the actual number of transducer elements will be further advanced in the future, reduction in the number of the transmission signal generating circuits 41 by half will contribute even more to the reduction of circuit size.

Further, in transfer of the aperture of an ultrasonic beam in the transducer element array direction, the transducer element connected to the transmission circuit is switched each time the aperture is transferred. In the switching operation of the transducer elements caused by the aperture transfer, the number of transmission circuits can be less than the entire number of elements.

Further, when considering a desired ultrasonic beam to be transmitted and the array direction of the transducer element is 2-dimensional, if the transmission signal generating circuits 41 in the array direction of the transducer element in rows can be used also in columns, the number of the transmission signal generating circuits 41 can be reduced by more than half of the number of 2-dimensionally arrayed transducer elements. In this manner, reduction of the number of transmission signal generating circuits 41 can contribute to further reduction of the circuit size.

On the other hand, if high-integration of the ultrasonic transmission/reception unit 4 is advanced, it is likely possible that the transmission signal generating circuits 41 are prepared for the same number of the entire transducer elements without using the HVSW 44.

The constant current source 45 stabilizes current I without depending on the measure of load impedance, and passes the DC component of the current passed from the source terminal of the FET 43 to the negative power source (Vss) from which the current is supplied to the FET 43. Also, the current source may be the current control type voltage source.

The sensitivity control circuit 46 has a function to adjust the gain of the reception signal, and supplies the signal to the FET 43. The sensitivity control circuit 46 includes a zener diode ZD that connects the positive power source (Vdd) of the power source and its own cathodic terminal, and variable resistor Rd to be connected in parallel to the cathodic terminal and anodic terminal of the zener diode ZD. Zener diode ZD is the element which can pass a current not only in the forward direction as a normal diode but also in the inverse direction if the inverse voltage is greater than the rated breakdown voltage referred to as "zener voltage". The constant voltage circuit is to be formed by using the characteristic of zener voltage. Variable resistor Rd is a device capable of varying the resistance value by the signal of the control unit 7, such as a digital potentiometer.

The ADC 47 inputs the reflected echo signal amplified by the gate grounding amplifier circuit including the FET 43 from the drain terminal of the FET 43 as an analogue signal, digitalizes and outputs the signal as the reflected echo data. The reflected echo data phased by the reception phasing circuit 422 is outputted to the ultrasonic image constructing unit 5.

Next, an operation example of the first embodiment from the transmission to the reception of ultrasonic waves will be described referring to FIG. 2.

An operation example for transmission of ultrasonic waves will be described below referring to FIG. 2(A).

An examiner sets a control parameter including information on an object such as the name and measurement information, e.g. a desired display depth using the control panel 8. The control unit 7 controls each component of the ultrasonic probe 3, the ultrasonic transmission/reception unit 4, the ultrasonic image constructing unit 5 and the display unit 6 based on the set control parameter. Also, the respective operations for transmission and reception of ultrasonic waves will be repeated according to a predetermined transmission/reception repetition frequency.

The control unit 7 causes the transmission phasing circuit 421 to input the AC voltage in the form of sine-wave, rectangular wave, etc. as a transmission signal 41*a*. The control unit 7 receives the set display depth in the object, and causes transmission phasing circuit 421 to focus the set transmission signal 41*a*. The output from the transmission phasing circuit 421 is to be inputted to the gate terminal of the FET 43. The output signal from the source terminal of the FET 43 is to be transmitted to one channel of a transducer 3*a* which constitutes the ultrasonic probe. The probe 3*a* receives the transmitted signal, and vibrates for transmitting the ultrasonic wave to the object. When the positive voltage is applied to the transducer 3*a*, the current is passed from Vdd to the transducer 3*a* via zener diode ZD, the drain terminal of the FET 43 and the source terminal. Also when the negative voltage is applied, the current is passed from the transducer 3*a* to the constant current source 45.

Next, an operation example upon reception of ultrasonic waves will be described referring to FIG. 2(B).

The control unit 7 causes the transmission phasing circuit 421 to input the DC voltage as a switch signal 41*b* for reception in order to set the operation mode upon transmitting an ultrasonic wave. The transmission phasing circuit 421 does not operate since it is in the reception mode, and the DC voltage is inputted to the gate terminal of the FET 43 as it is. The FET 43 receives the supply of the DC voltage to its own gate terminal, and functions as the gate grounding amplifier. The control unit 7 sets the transmission gate of the FET 43 (gate grounding amplifier) to variable the resistor Rd of the sensitivity control circuit 46.

The transducer 3*a* receives the reflected echo signal from the object. The received reflected echo signal is transmitted to the source terminal of the FET 43. The FET 43 amplifies the reflected echo signal transmitted to its own source terminal by the transmission gate obtained by multiplying its own equivalent conductance gm by variable resistor Rd in the sensitivity control circuit 46, and outputs the reflected echo signal amplified by its own drain terminal to the ADC 47. The ADC 47 inputs the amplified reflected echo signal as an analogue signal, digitalizes and outputs the signal as the reflected echo data. The control unit 7 receives the set display depth in the object, and causes reception phasing circuit 422 to focus the reflected echo data. The reflected echo data phased by the reception phasing circuit 422 is outputted to the ultrasonic image constructing unit 5. Further, the ultrasonic image constructing unit 5 constructs an ultrasonic image based on the reception signal. The display unit 6 displays the ultrasonic image constructed by the ultrasonic image constructing unit 5.

While the above-described operation example executes phasing both on the transmission side and the reception side, the phasing may be executed only in one of the transmission side or the reception side.

In accordance with the above-described first embodiment of the present invention, since the FET 43 can execute the function to supply the signal to transducer 3*a* upon transmission and the function to amplify the echo signal upon reception by one element, the conventional need for providing a reception circuit and a transmission circuit separately can be eliminated, whereby making it possible to reduce the circuit size of the ultrasonic transmission/reception unit more than by the conventional technique. Also, the characteristic effect of the first embodiment is that the number of elements used in the main circuit components can be reduced to only the transmission signal generating unit 41, the FET 43, the sensitivity control circuit 46 and the ADC 47, whereby contributing to reduction of the circuit size.

Embodiment 2

The configuration example and the operation example of the ultrasonic transmission/reception unit in the second embodiment related to the present invention will be described referring to FIG. 3.

Figure 3:
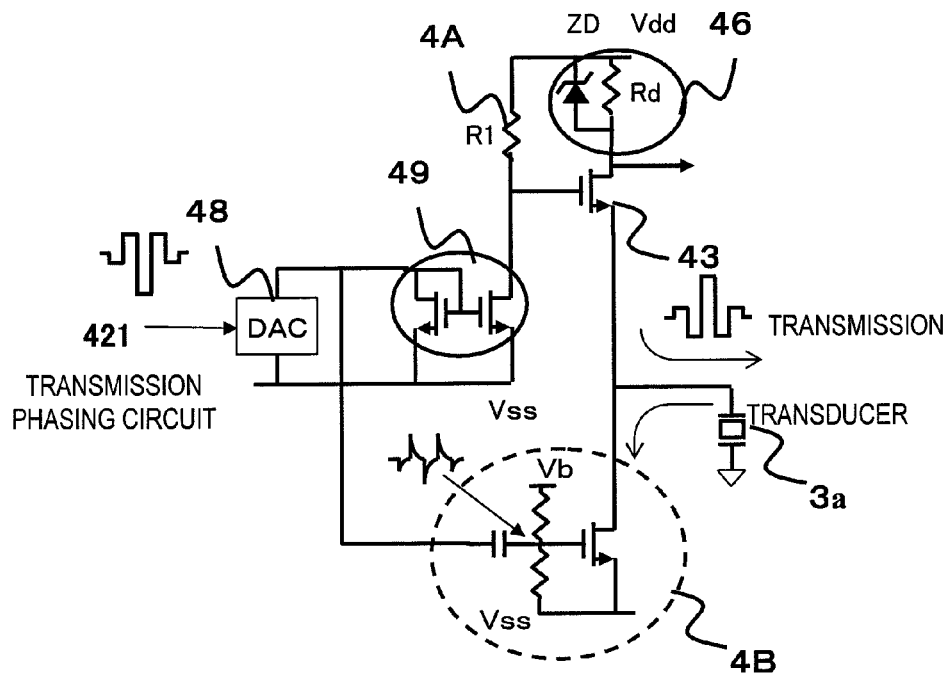
FIG. 3 is a circuitry diagram and an operation diagram of embodiment 2 related to the present invention.
Figure 3:
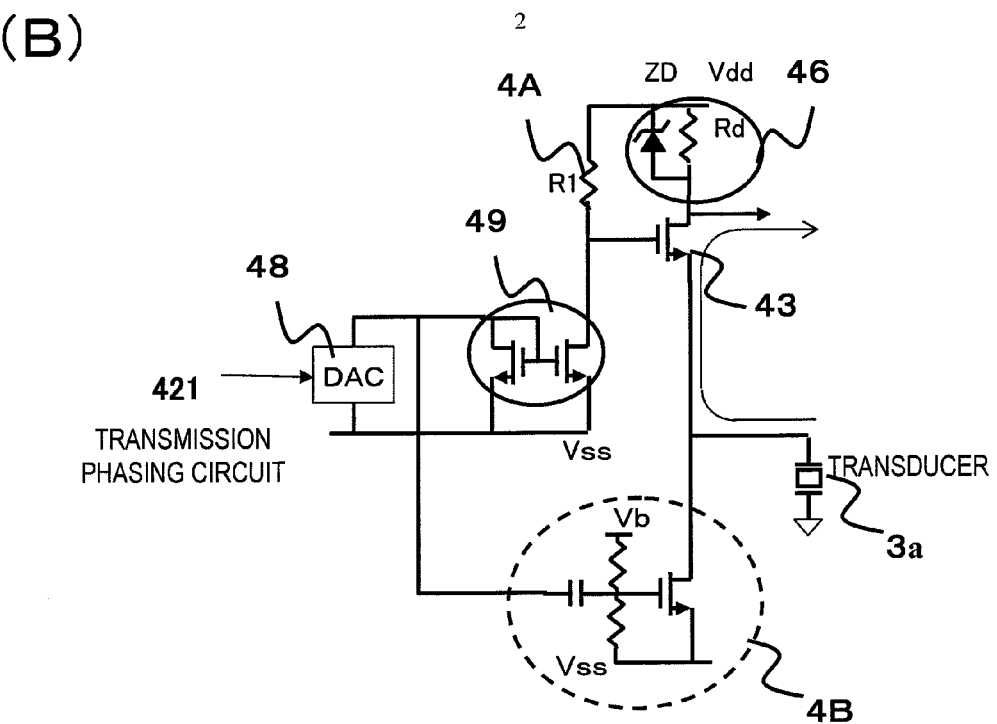

FIG. 3 is a circuitry diagram and operation diagram of the second embodiment in the present invention. FIG. 3(A) which is the variation diagram of FIG. 2 shows the operation diagram upon transmission of an ultrasonic wave, and FIG. 3(B) shows the operation diagram upon reception of an ultrasonic wave.

The ultrasonic transmission/reception unit 4 shares the transmission signal generating unit 41, the phasing circuit 42, the FET 43 and the sensitivity control circuit 46 with the first embodiment, and the additional or modified parts in the present embodiment are a digital analogue converter (DAC) 48, a current mirror circuit 49, a resistor 4A and a differentiation circuit 4B.

Description of the parts in the respective components which are the same as the first embodiment will be omitted, and only the additional or modified parts will be described.

The DAC 48 converts the digital data of the ultrasonic signal to be transmitted which is focused by the digital phasing method into the analogue digital ultrasonic signal.

The current mirror circuit 49 is connected to the DAC 48, and the ultrasonic signal in the same phase as the DAC 48 is outputted to the gate terminal of the FET 43. This is because the output current as the element of the DAC 48 cannot reach the driving current which is sufficient enough to drive the transducer 3*a*, since the AC signal to be supplied to the gate terminal of the FET 43 is outputted to the transducer 3*a* as it is. Given this factor, the driving current necessary for driving transducer 3*a* in the FET of the output current side is obtained by short-circuiting the respective gate terminals of the FET on the input current side and the FET on the output side of the current mirror circuit 49.

The resistor 4A is provided for biasing the output signal of the FET on the output current side of current mirror circuit 49.

The differentiation circuit 4B is provided to the source terminal of the FET 43, acquires the detection signal for passing the current from the transducer 3*a* only upon falling of the transmission signal, and transmits the detection signal to the control unit 7.

Next, the example of the operation from transmission to reception of an ultrasonic wave in the first embodiment will be described referring to FIG. 3.

The operation example upon transmission of an ultrasonic wave will be described referring to FIG. 3(A).

An examiner sets the control parameter including object information such as the name or measurement information, e.g. a desired display depth using the control panel 8. The control unit 7 controls the respective components of the ultrasonic probe 3, the ultrasonic transmission/reception unit 4, the ultrasonic image constructing unit 5 and the display unit 6 based on the set control parameter. Also, the respective operations upon transmission and reception of an ultrasonic wave are repeated in accordance with a predetermined transmitting/receiving repetition frequency.

The control unit 7 causes the transmission phasing circuit 421 to input the AC voltage in the form of a sine-wave or rectangular wave, etc. as the transmission signal 41a. The control unit 7 receives the set display depth of the object, and causes the transmission phasing circuit 421 to focus the set transmission signal 41a. The output signal from the transmission phasing circuit 421 is inputted to the gate terminal of the FET 43. The output signal from the source terminal of the FET 43 is transmitted to one channel of the transducer 3a which constitutes the ultrasonic probe. The transducer 3a vibrates upon receiving the transmitted signal, and transmits an ultrasonic wave to the object. Here, the current is passed from Vdd to the transducer 3a via zener diode ZD, the drain terminal of the FET 43 and the source terminal as in the first embodiment when the positive voltage is applied to the transducer 3a. The current is passed from the transducer 3a to the FET 43 as in the first embodiment when the negative voltage is applied to the transducer 3a, but in the present embodiment the current is passed from transducer 3a only upon falling of the ultrasonic signal transmitted from the differentiation circuit 4B provided to the source terminal of the FET 43. Therefore, it is possible to suppress the electric power consumption for driving the transducer 3a compared to the normal power distribution in the first embodiment.

Next, the operation example upon receiving an ultrasonic wave will be described referring to FIG. 3(B).

The control unit 7 causes the transmission phasing circuit 421 to input the DC voltage as the switch signal 41b for reception in order to set the operation mode for ultrasonic-wave transmission. The transmission phasing circuit 421 does not operate since it is reception, and the DC voltage is inputted to the gate terminal of the FET 43 as it is. The FET 43 receives the supply of the DC voltage to its own gate terminal, and functions as the gate grounding amplifier. The control unit 7 sets the transmission gate of the FET 43 (gate grounding amplifier) to the variable resistor Rd of the sensitivity control circuit 46.

The transducer 3a receives the reflected echo signal from the object. The received reflected echo signal is transmitted to the source terminal of the FET 43. The FET 43 amplifies the reflected echo signal transmitted to its own source terminal by the transmission gate acquired by multiplying its own equivalent conductance gm by the variable resistor Rd in the sensitivity control circuit 46, and outputs the reflected echo signal amplified by its own drain terminal to the ADC 47. The ADC 47 inputs the amplified reflected echo signal as an analogue signal, and digitalizes and outputs the signal as the reflected echo data. The control unit 7 receives the set display depth in the object, and causes transmission phasing circuit 421 to focus the reflected echo data. The reflected echo data phased by the reception phasing circuit 422 are outputted to the ultrasonic image constructing unit 5. Further, the ultrasonic image constructing unit 5 constructs an ultrasonic image based on the reception signal. The display unit 6 displays the ultrasonic image constructed in the ultrasonic image constructing unit 5.

While the above-described operation example executes phasing both on the transmission side and the reception side, the phasing may be executed in only one of the transmission side or the reception side.

In accordance with the above-described the second embodiment of the present invention, since the FET 43 can execute the function to supply the transmission signal to the transducer 3a upon transmission and the function to amplify the echo signal upon reception by one element, the conventional need for providing a reception circuit and a transmission circuit separately can be eliminated, whereby making it possible to reduce the circuit size of the ultrasonic transmission/reception unit more than the conventional technique. The characteristic effect of second embodiment is that the electric power consumption can be reduced since the current to be passed to a transducer for transmission is turned on only on the trailing edge of the transmission waveform. In other words, since heat generation in the circuit can be suppressed, the circuit elements can be disposed close to each other, whereby contributing to reduction of the circuit size.

Embodiment 3

Figure 4:
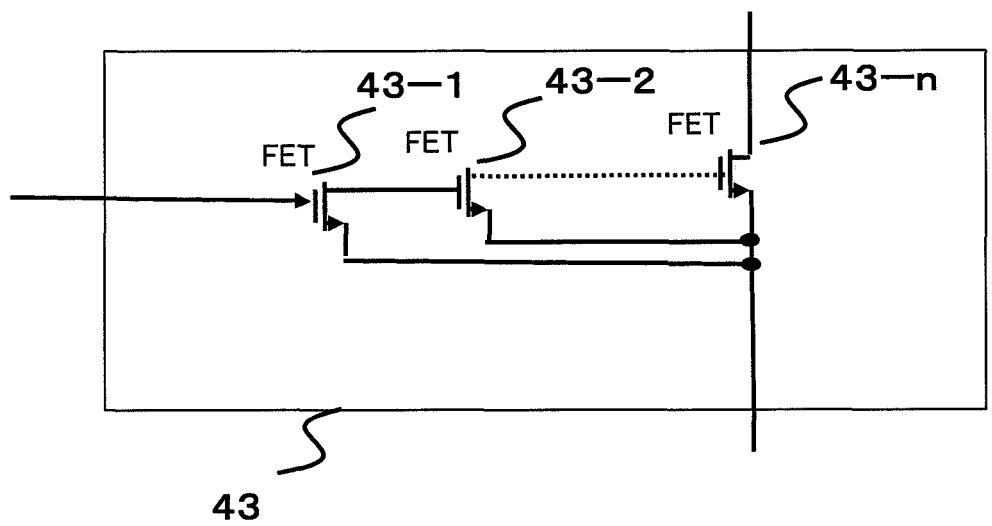
FIG. 4 is a circuitry diagram and an operation diagram of embodiment 3 related to the present invention.

While FET having one stage is used to achieve the first embodiment or the second embodiment, resistance to high voltage still remains as a problem to be solved. The third embodiment will be exemplified below for saving electric power using multistage connection of FET with low voltage of about 5V referring to FIG. 4. FIG. 4 is a circuit configuration diagram and an operation diagram of third embodiment related to the present invention.

As shown in FIG. 4, the FET 43-1, FET 43-2, . . . , and FET 43-n with low voltage of about 5V are connected using multistage connection. The Darlington connection which increases the current amplification factor of the transistor can be used as the multistage connection method. Though gm cannot be increased by implementing Darlington connection on the FET, it is possible to lower the input impedance of the element to be connected as the output load of the FET in the case that the FET is used as the source follower circuit as in the present invention.

In accordance with the above-described the third embodiment of the present invention, since the FET 43 can execute the function to supply the transmission signal to the transducer 3a upon transmission and the function to amplify the echo signal upon reception by one element, the conventional need for providing the reception circuit and the transmission circuit separately can be eliminated, whereby making it possible to reduce the circuit size of the ultrasonic transmission/reception unit more than the conventional technique.

Also, the characteristic effect of embodiment 3 is that application of the power source for Vdd and Vss can be skipped upon reception and the circuit can be operated with the lower voltage power source of about 5V, whereby making it possible to configure the reception circuit with a lower voltage FET.

Also, since a multistage FET is connected using the Darlington connection, the input impedance of the element to be connected as the output load of the FET can be lowered and the noise of the gate grounding amplifier can also be lowered.

While the semiconductor circuit element is explained using the field-effect transistor in the above-described respective embodiments, any kind of semiconductor circuit element such as a bipolar transistor can be used as long as it has at least 3 terminals and the function to amplify electric signals is provided between any of the 2 terminals.

In the case that a bipolar transistor is used for the semiconductor circuit element, for example the collector terminal is connected to a plurality of transducer elements that constitute an ultrasonic probe, a transmission signal generating circuit is connected to the base terminal, and the emitter terminal is to be the output terminal of an amplifier for a reception signal from the transducer element.

Also, the transducer for an ultrasonic probe may be a piezoelectric element or a CMUT (Capacitive Micro-Machined Ultrasonic Transducer).

INDUSTRIAL APPLICABILITY

The present invention can be applied to an ultrasonic diagnostic apparatus for the use of livestock industry and nondestructive inspections.

DESCRIPTION OF REFERENCE NUMERALS

4: ultrasonic transmission/reception unit, 41: transmission signal generating unit, 42: phasing circuit, 43: field-effective transistor (FET), 46: sensitivity control circuit

The invention claimed is:

1. An ultrasonic transmission/reception circuit comprising:
    a semiconductor circuit element including at least three terminals of a first terminal connected to a plurality of transducer elements that constitute an ultrasonic probe, a second terminal connected to a transmission signal generating circuit and a third terminal serving as an output terminal of an amplifier of a reception signal from the transducer element, and has a function of amplifying a signal inputted from one terminal by the other terminal and outputting the amplified signal between at least two terminals among the above-mentioned three terminals; and
    a control unit which performs control so as to cause the semiconductor circuit element to respectively perform a first function as a switch for inputting a transmission signal to the transducer element and a second function to amplify the reception signal from the transducer element.

2. The ultrasonic transmission/reception circuit according to claim 1, characterized in that the semiconductor circuit element is a field-effect transistor element which connects the source terminal to a plurality of transducer elements that constitute an ultrasonic probe, connects a transmission signal generating circuit to the gate terminal and causes the drain terminal to be the output terminal of an amplifier of a reception signal from the transducer element.

3. The ultrasonic transmission/reception circuit according to claim 2, characterized in that the field-effect transistor element is an NMOS-type FET.

4. The ultrasonic transmission/reception circuit according to claim 1, characterized in that the semiconductor circuit element is a bipolar transistor element which connects the collector terminal to a plurality of transducer elements that constitute an ultrasonic probe, connects a transmission signal generating circuit to the base terminal and causes the emitter element to be the output terminal of an amplifier of a reception signal from the transducer element.

5. The ultrasonic transmission/reception circuit according to claim 1, characterized in further comprising a switch unit which supplies an ultrasonic signal from one of the outputs of the transmission signal generating unit to a plurality of transducer elements, so that the control unit can supply an ultrasonic signal for transmission to all elements of the transducer.

6. The ultrasonic transmission/reception circuit according to claim 1, characterized in further comprising a detection unit configured to detect a detection signal for passing a current to a transducer only in a predetermined period when a signal is transmitted from the transmission signal generating circuit.

7. The ultrasonic transmission/reception circuit according to claim 2, characterized in that the semiconductor circuit element is formed by transistor elements that are multi-element being connected by the Darlington connection.

8. An ultrasonic diagnostic apparatus of the present invention comprising:
    an ultrasonic probe configured to transmit/receive ultrasonic waves to/from an object to be examined;
    an ultrasonic transmission/reception unit configured to drive the ultrasonic probe and performs signal processing on a reflected echo signal received from the ultrasonic probe;
    an ultrasonic image construction unit configured to construct an ultrasonic image using signal-processed reflected echo signals;
    a display unit configured to display the ultrasonic image;
    a control unit configured to control respective units from the ultrasonic probe to the display unit; and
    a setting unit configured to perform setting of control conditions for the respective units to the control unit,
    wherein the ultrasonic transmission/reception unit has a semiconductor circuit element which has at least three terminals including a first terminal connected to a plurality of transducer elements that constitute the ultrasonic probe, a second terminal connected to a transmission signal generating circuit and a third terminal serving as an output terminal of an amplifier of a reception signal from a transducer element of the plurality of transducer elements, and has a function to amplify a signal inputted to one terminal by an other terminal and outputting an amplified signal between at least two terminals of the at least three terminals, and the semiconductor circuit element shares a first function with a second function, wherein the first function includes a switch for inputting a transmission signal to one channel of the transducer element and the second function includes amplifying the reception signal received from one channel of the transducer element, and
    wherein the control unit is further configured to controls the semiconductor circuit so as to perform the first function and the second function.

9. The ultrasonic diagnostic apparatus according to claim 8, wherein the control unit is further configured to vary a transmission terminal of amplification of the reception signal in the second function in accordance with a display depth of the ultrasonic image set by the setting unit.

10. The ultrasonic diagnostic apparatus according to claim 8, wherein the semiconductor circuit element is an field-effect transistor element which connects the source terminal to a plurality of transducers that constitute the ultrasonic probe, connects the transmission signal generating circuit to a gate terminal and causes a drain terminal to be the output terminal of the amplifier of the reception signal from the transducer element.

11. The ultrasonic diagnostic apparatus according to claim 10, wherein the field-effect transistor element is an NMOS-type FET.

12. The ultrasonic diagnostic apparatus according to claim 8, wherein the semiconductor circuit element is a bipolar transistor element which connects a collector terminal to a plurality of transducers that constitute the ultrasonic probe, connects the transmission signal generating circuit to a base terminal and causes an emitter terminal to be the output terminal of the amplifier of the reception signal from the transducer element.

13. The ultrasonic diagnostic apparatus according to claim 8, further comprising:
    a switching unit which supplies an ultrasonic signal from one of the outputs of the transmission signal generating unit to a plurality of transducer elements, so that the control unit can supply an ultrasonic signal for transmission to all elements of the transducer.

14. The ultrasonic diagnostic apparatus according to claim 8, further comprising:
a detection unit configured to detect a detection signal for passing a current to a transducer only in a predetermined period when a signal is transmitted from the transmission signal generating circuit.

15. The ultrasonic diagnostic apparatus according to claim 8, wherein the semiconductor circuit element is formed by transistor elements that are multi-element being connected by a Darlington connection.

\* \* \* \* \*